(12) United States Patent
Sasaki

(10) Patent No.: US 12,247,002 B2
(45) Date of Patent: Mar. 11, 2025

(54) PROCESS AND APPARATUS FOR UREA PRODUCTION

(71) Applicant: TOYO ENGINEERING CORPORATION, Tokyo (JP)

(72) Inventor: Keigo Sasaki, Narashino (JP)

(73) Assignee: Toyo Engineering Corporation, Tokyo (JP)

( * ) Notice: Subject to any disclaimer, the term of this patent is extended or adjusted under 35 U.S.C. 154(b) by 850 days.

(21) Appl. No.: 17/438,915

(22) PCT Filed: Mar. 14, 2019

(86) PCT No.: PCT/JP2019/010610
§ 371 (c)(1),
(2) Date: Sep. 13, 2021

(87) PCT Pub. No.: WO2020/183717
PCT Pub. Date: Sep. 17, 2020

(65) Prior Publication Data
US 2022/0185772 A1    Jun. 16, 2022

(51) Int. Cl.
*C07C 273/04*    (2006.01)
*B01D 5/00*    (2006.01)
(Continued)

(52) U.S. Cl.
CPC .......... *C07C 273/04* (2013.01); *B01D 5/0012* (2013.01); *B01D 19/0068* (2013.01);
(Continued)

(58) Field of Classification Search
None
See application file for complete search history.

(56) References Cited

U.S. PATENT DOCUMENTS

| 5,936,122 A | 8/1999 | Kojima et al. |
| 6,200,540 B1 | 3/2001 | Kojima et al. |

(Continued)

FOREIGN PATENT DOCUMENTS

| CN | 1617853 A | 5/2005 |
| CN | 101166714 A | 4/2008 |

(Continued)

OTHER PUBLICATIONS

Office Action issued in Pakistan Application No. 171/2020, dated Oct. 9, 2020.
International Search Report and Written Opinion issued in International Patent Application No. PCT/JP2019/010610, dated Nov. 26, 2019.

(Continued)

*Primary Examiner* — Amy C Bonaparte
(74) *Attorney, Agent, or Firm* — Foley & Lardner LLP

(57) ABSTRACT

In a urea synthesis process, temperature distribution in a submerged condenser is reduced. The process includes: synthesizing urea from $NH_3$ and $CO_2$ to generate a urea synthesis solution; by heating the solution, decomposing ammonium carbamate and separating a gaseous mixture containing $NH_3$ and $CO_2$ from the solution to obtain a solution higher in urea concentration than the solution obtained in the synthesizing; with use of a submerged condenser including a shell and tube heat exchange structure including a U-tube, absorbing and condensing at least a part of the gaseous mixture in an absorption medium on a shell side, and generating steam on a tube side with use of heat generated during the condensation; and recycling at least a part of liquid, obtained from the shell side, to the synthesizing, wherein water is supplied to the tube side of the condenser at a mass flow rate that is three times or more of the steam generation rate.

9 Claims, 1 Drawing Sheet

(51) Int. Cl.
  *B01D 19/00* (2006.01)
  *B01D 53/18* (2006.01)
  *B01J 19/24* (2006.01)

(52) U.S. Cl.
  CPC .......... *B01D 53/18* (2013.01); *B01J 19/2465* (2013.01); *B01J 2219/00092* (2013.01); *B01J 2219/00164* (2013.01)

(56) References Cited

U.S. PATENT DOCUMENTS

| | | |
|---|---|---|
| 6,518,457 B1 | 2/2003 | Sakata et al. |
| 2006/0270872 A1 | 11/2006 | Kojima |
| 2009/0036712 A1 | 2/2009 | Kojima |
| 2009/0062566 A1 | 3/2009 | Kojima |
| 2010/0063321 A1 | 3/2010 | Zardi et al. |

FOREIGN PATENT DOCUMENTS

| | | |
|---|---|---|
| CN | 101166715 A | 4/2008 |
| CN | 101558037 A | 10/2009 |
| EP | 0 155 735 A1 | 9/1985 |
| EP | 1 728 783 A1 | 12/2006 |
| EP | 1 876 171 A1 | 1/2008 |
| JP | H10-182587 A | 7/1998 |
| JP | 2003-104949 A | 4/2003 |
| SU | 1456009 A3 | 1/1989 |
| WO | WO 03/064379 A1 | 8/2003 |
| WO | WO 2006/118071 A1 | 11/2006 |
| WO | WO 2013/165246 A1 | 11/2013 |

OTHER PUBLICATIONS

Office Action and Search Report issued in Russian Patent Application No. 2021129736, dated Jul. 4, 2022.
Office Action and Search Report issued in Chinese Patent Application No. 201980093977.3, dated Sep. 27, 2022.

[Fig. 1]
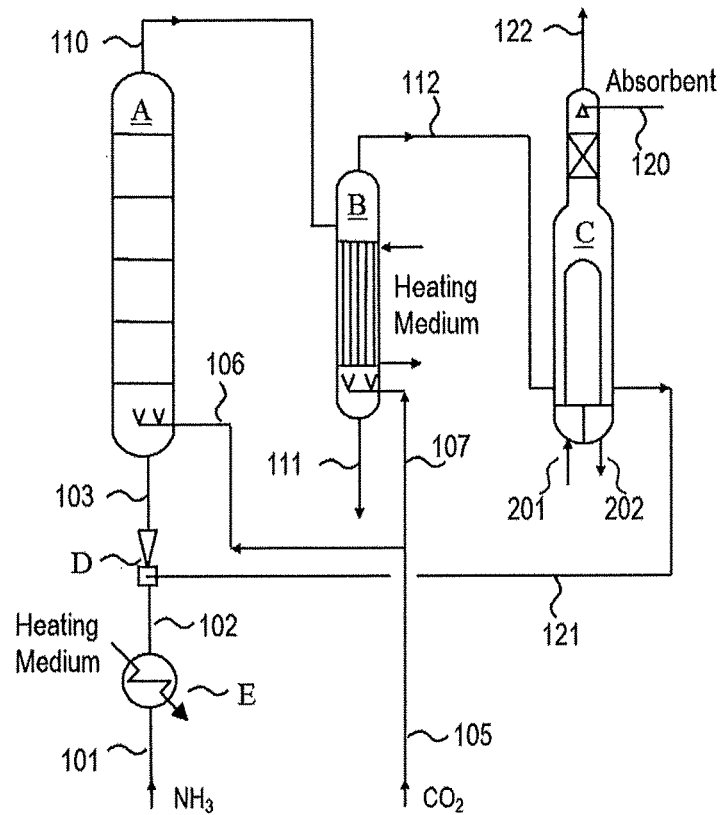
[Fig. 2]
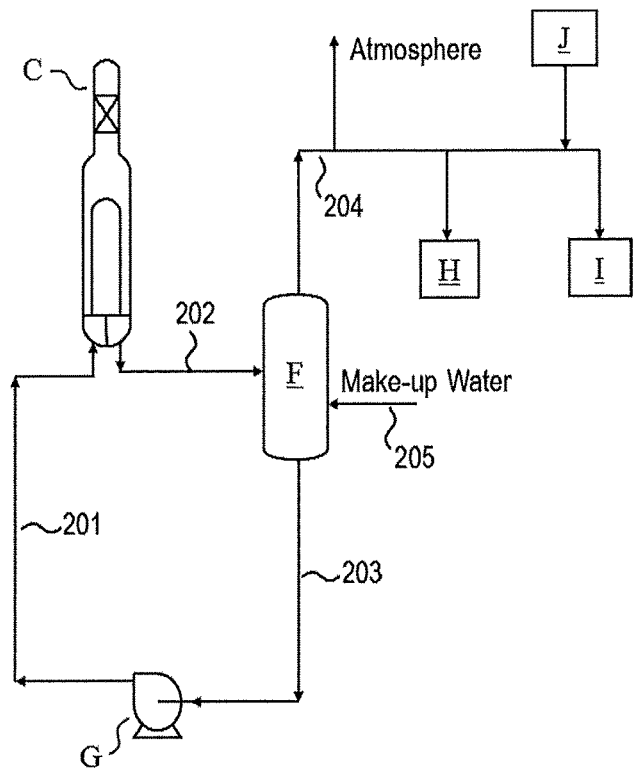

PROCESS AND APPARATUS FOR UREA PRODUCTION

CROSS-REFERENCE TO RELATED APPLICATION

This application is the U.S. National Stage of International Patent Application No. PCT/JP2019/010610, filed Mar. 14, 2019. The contents of this application is incorporated herein by reference in its entirety.

TECHNICAL FIELD

The present invention relates to a process and apparatus for producing urea from ammonia and carbon dioxide.

BACKGROUND ART

A process for urea production typically includes a synthesis step, a decomposition step, and a condensation step. In the synthesis step, urea is synthesized from ammonia ($NH_3$) and carbon dioxide ($CO_2$) to generate a urea synthesis solution. Specifically, as shown by Formula (1), ammonium carbamate ($NH_2COONH_4$) is generated by the reaction of ammonia ($NH_3$) and carbon dioxide ($CO_2$). Furthermore, as shown by Formula (2), urea ($NH_2CONH_2$) and water ($H_2O$) are generated by a dehydration reaction of ammonium carbamate.

$$2NH_3 + CO_2 \rightarrow NH_2COONH_4 \quad (1)$$

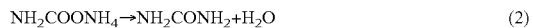
$$NH_2COONH_4 \rightarrow NH_2CONH_2 + H_2O \quad (2)$$

While both the reactions are equilibrium reactions, the reaction of Formula (2) is rate-determining as it is slower than the reaction of Formula (1).

In the decomposition step, the urea synthesis solution obtained in the synthesis step is heated to decompose the ammonium carbamate contained in the urea synthesis solution into ammonia and carbon dioxide. As a result, a gaseous mixture containing ammonia and carbon dioxide, and a urea synthesis solution having a higher urea concentration are obtained. In the condensation step, the gaseous mixture obtained in the decomposition step is condensed in an absorption medium under cooling. Water is often used as a cooling medium used for the cooling, and the gaseous mixture is cooled mainly with the latent heat of vaporization of water.

JP10-182587A (corresponding to EP 0834501 A2, EP 1035111 A1, EP 1035112 A1, U.S. Pat. Nos. 5,936,122 A and 6,200,540 B1) discloses a condensation step involving use of a vertical submerged condenser including U-tubes as cooling tubes, with a cooling medium being fed to a tube side of the vertical submerged condenser. In general, a submerged condenser refers to a condenser in which a process fluid flows on the shell side, in other words, a gaseous mixture obtained in the decomposition step is supplied to the process side, and in which a cooling medium flows on the tube side. Letting the process fluid flow on the shell side can lengthen the residence time of the process fluid in the condenser. This is effective for promoting the generation reaction of urea in the condenser.

JP2003-104949A (corresponding to EP 1279663 A1 and U.S. Pat. No. 6,518,457 B1) also discloses a vertical submerged condenser including U-tubes as cooling tubes. This literature discloses a technique of recovering the heat of condensation by generating low-pressure steam in some of the U-tubes and by heating a urea synthesis solution obtained from a stripper (decomposition step) in the remaining U-tubes. WO 2013/165246 discloses similar technique, though a horizontal submerged condenser is disclosed in this document. WO 2006/118071 (corresponding to EP 1876171 A1 and US 2009/062566 A1) also discloses a vertical submerged condenser including U-tubes. In this literature, a fluid containing boiler water and steam is discharged from the U-tubes.

CITATION LIST

Patent Literature

PTL 1: JP10-182587A
PTL 2: JP2003-104949A
PTL 3: WO 2013/165246
PTL 4: WO 2006/118071

SUMMARY OF INVENTION

Technical Problem

Although heat recovery in the submerged condenser has conventionally been studied as stated above, attention has been paid to the process and apparatus for letting the process fluid flow, but not to a process and apparatus for letting the cooling medium flow.

In a submerged condenser, it is desirable to promote not only the condensation of the gaseous mixture obtained in the decomposition step but also the generation reaction of urea. An operating temperature of the submerged condenser is preferably higher from a viewpoint of promoting the urea generation in the submerged condenser, whereas the operating temperature is preferably lower from a viewpoint of promoting the absorption of the gas. Therefore, it is desired to maintain the entire inside of the submerged condenser at an optimum operating temperature. For this reason, it is desired to reduce temperature distribution in the submerged condenser.

In the case of supplying water, in an amount (mass flow rate) that is comparable to the amount of steam generated on the tube side of the submerged condenser, to the tube side as a cooling medium, water (liquid) flows at the inlet of the tube, while mainly steam (gas) flows at the outlet. In this case, the cooling effect by the latent heat of vaporization of water at the tube outlet is smaller than that at the tube inlet. Therefore, the heat exchange amount is different between the vicinity of the tube inlet and the vicinity of the tube outlet. As a result, a temperature difference is generated between these regions, which increases the temperature distribution in the submerged condenser.

An object of the present invention is to provide a process and apparatus for urea synthesis, capable of reducing temperature distribution in a submerged condenser.

Solution to Problem

An aspect of the present invention provides a process for urea production, comprising:
a synthesis step of synthesizing urea from ammonia and carbon dioxide to generate a urea synthesis solution;
a decomposition step of, by heating the urea synthesis solution generated in the synthesis step, decomposing ammonium carbamate and separating a gaseous mixture containing ammonia and carbon dioxide from the urea synthesis solution to obtain a urea synthesis solution which is higher in urea concentration than the urea synthesis solution obtained in the synthesis step;

a condensation step of, with use of a submerged condenser including a shell and tube heat exchange structure including a U-tube, absorbing and condensing at least a part of the gaseous mixture obtained in the decomposition step in an absorption medium on a shell side, and generating steam on a tube side with use of heat generated during the condensation;

a recycling step of recycling at least a part of a liquid, said liquid being obtained from the shell side in the condensation step, to the synthesis step; and a water supply step of supplying water to the tube side of the submerged condenser at a mass flow rate that is three times or more of a generation rate of the steam generated in the submerged condenser.

Another aspect of the present invention provides an apparatus for urea production, comprising:

a synthesis reactor configured to synthesize urea from ammonia and carbon dioxide to generate a urea synthesis solution;

a decomposer configured to, by heating the urea synthesis solution generated by the synthesis reactor, decompose ammonium carbamate and separating a gaseous mixture containing ammonia and carbon dioxide from the urea synthesis solution, to obtain a urea synthesis solution which is higher in urea concentration than the urea synthesis solution obtained by the synthesis reactor;

a submerged condenser including a shell and tube heat exchange structure containing a U-tube, the submerged condenser being configured to absorb and condense at least a part of the gaseous mixture obtained by the decomposer in an absorption medium on a shell side, and generate steam on a tube side with use of heat generated during the condensation; densation;

a recycling means for recycling at least a part of liquid, said liquid being obtained from the shell side of the submerged condenser, to the synthesis reactor; and a water supply means for supplying water to the tube side of the submerged condenser at a mass flow rate that is three times or more of a generation rate of the steam generated in the submerged condenser.

Advantageous Effects of Invention

The present invention provides a process and apparatus for urea synthesis, capable of reducing temperature distribution in a submerged condenser.

BRIEF DESCRIPTION OF DRAWINGS

FIG. 1 is a process flow diagram schematically showing an example of an apparatus for urea production.

FIG. 2 is a process flow diagram schematically showing an example of a cooling system (steam system) of a submerged condenser.

DESCRIPTION OF EMBODIMENTS

A process for urea production according to the present invention includes a synthesis step, a decomposition step, a condensation step, and a recycling step. Ammonia and carbon dioxide as raw materials can be supplied, as appropriate, to one or more of these steps from the outside. The process for urea production further includes a water supply step.

Synthesis Step

In the synthesis step, urea is synthesized from ammonia and carbon dioxide to generate a urea synthesis solution. In the synthesis step, urea is also synthesized from ammonium carbamate contained in a recycled liquid from a condensation step that will be described later.

An operating pressure in the synthesis step is typically 130 bars (absolute pressure, which also applies to the following description) to 250 bars, preferably 140 bars to 200 bars. The operating temperature of the synthesis step is typically 160° C. to 200° C., preferably 170° C. to 190° C.

Decomposition Step

In the decomposition step, the urea synthesis solution generated in the synthesis step is heated. Hence, ammonium carbamate contained in the urea synthesis solution obtained in the synthesis step is decomposed, and a gaseous mixture containing ammonia and carbon dioxide is separated from the urea synthesis solution to obtain a urea synthesis solution which is higher in urea concentration than the urea synthesis solution obtained in the synthesis step. The gaseous mixture obtained in the decomposition step may hereinafter be referred to as "decomposer outlet gas."

For the heating in the decomposition step, a heating medium having a relatively high temperature, for example, medium-pressure steam, can be utilized. In this case, the medium-pressure steam, which is used as a heat source, condenses to generate steam condensate.

The pressure of the medium-pressure steam is typically 12 bars to 40 bars, preferably 14 bars to 25 bars. The medium-pressure steam is often appropriately generated as back-pressure steam of a steam turbine in an apparatus for urea production. Alternatively, the medium-pressure steam may be supplied from the outside of the apparatus for urea production.

The operating temperature of the decomposition step is typically 150° C. to 220° C., preferably 160° C. to 200° C.

Specifically, the urea synthesis solution obtained in the synthesis step contains urea, ammonia, carbon dioxide, ammonium carbamate, and water. The urea synthesis solution is usually heated under the pressure which is substantially equal to the pressure in the synthesis step. As a consequence, ammonia, carbon dioxide, and ammonium carbamate are separated as a gaseous mixture containing ammonia, carbon dioxide, and water (steam).

In the decomposition step, it is possible to adopt a decomposition method in which only the heating is performed. However, in order to promote the decomposition, it is possible to adopt a stripping process in which, in addition to the heating, carbon dioxide gas is supplied and is brought into contact with the urea synthesis solution.

Condensation Step

In the condensation step, a submerged condenser including a shell and tube heat exchange structure is used. The shell and tube heat exchange structure includes a U-tube. Usually, there are a plurality of U-tubes, which form a so-called multitubular heat exchange structure. On the shell side of the heat exchange structure, at least a part of, that is, a part or the entire of the gaseous mixture (decomposer outlet gas) obtained in the decomposition step is absorbed and condensed in an absorption medium. With the heat generated during the condensation, steam is generated on the tube side.

Here, steam, for example, low-pressure steam, can be generated. When the condensation temperature is taken into consideration, the low-pressure steam should have a pressure under which the saturation temperature of water is lower than the temperature of the process fluid in the condensation step. In consideration of utilizing the generated low-pressure steam in another step of the process for urea production, the pressure of the low-pressure steam is preferably high to some extent. From such viewpoints, the pressure of the low-pressure steam is typically 3 bars to 9 bars, preferably 4 bars to 7 bars. When the low-pressure steam is used as a heat source for heating another fluids, the low-pressure steam condenses, which generates steam condensate.

As the absorption medium, an absorption medium publicly known in the field of the process for urea production, such as water (which may contain urea, ammonia, carbon dioxide, and ammonium carbamate), can appropriately be used.

The temperature of the liquid obtained on the shell side in the condensation step is typically 100° C. to 210° C., preferably 160° C. to 190° C. when the balance between the reaction and the condensation is taken into consideration in particular. The synthesis step, the decomposition step, and the condensation step are operated at the substantially same pressure, since the high-pressure process (including the synthesis step, the decomposition step, and the condensation step) in urea production has nothing which results in pressure reduction except pressure loss. Note that pressurization by an ejector or the like is performed for the recycling which will be described later.

More specifically, the gaseous mixture (decomposer outlet gas) separated in the decomposition step is introduced into the condensation step, where the gaseous mixture comes into contact with the absorption medium containing water under cooling, and where the gaseous mixture condenses. In the condensation step, a part of ammonia and a part of carbon dioxide turn into ammonium carbamate (see Formula (1)), and urea synthesis reaction (see Formula (2)) also progresses.

When the gaseous mixture condenses in the condensation step, a large amount of heat is generated. To effectively use the generated heat, heat recovery is performed. That is, with the heat generated during the condensation, steam is generated on the tube side. For this purpose, the process for urea production includes a water supply step of supplying water (liquid) to the tube side of the submerged condenser.

The gas not condensed on the shell side of the submerged condenser, after being reduced in pressure as necessary, may be absorbed and condensed in an absorption medium (liquid), and simultaneously the absorption medium may be cooled. Thus, a recovered liquid containing ammonia and carbon dioxide can be obtained. The recovered liquid may be pressurized as necessary, and then may be returned to the high-pressure process (including the synthesis step, the decomposition step, and the condensation step), typically to the condensation step. Thus, unreacted ammonia and unreacted carbon dioxide can be recovered. As the absorption medium, an absorption medium publicly known in the field of the process for urea production, such as water (which may contain urea, ammonia, carbon dioxide, and ammonium carbamate), can appropriately be used.

Water Supply Step

In the water supply step, water (liquid) is supplied to the tube side of the submerged condenser. In this operation, the mass flow rate of the water to be supplied is three times or more, preferably eight times or more of the amount (generation rate on a mass basis) of the steam generated on the tube side of the submerged condenser. Accordingly, a ratio of the water (liquid) in the cooling medium (a gas-liquid two-phase flow made of water and steam) at the U-tube outlet can be kept relatively high. As a result, a difference between a heat exchange amount in the vicinity of the U-tube inlet and a heat exchange amount in the vicinity of the U-tube outlet can be reduced. Therefore, temperature distribution in the submerged condenser can be reduced. When the mass flow rate of the water to be supplied exceeds 25 times the amount of the steam generated on the tube side of the submerged condenser, it is hard to expect the effect of further reduction of the temperature distribution even if the mass flow rate of water is further increased.

From a viewpoint of efficient heat-exchange, the flow speed at the U-tube inlet of the water supplied to the tube side of the submerged condenser is preferably 0.3 m/s or more, more preferably 0.8 m/s or more. However, as the flow speed is set higher, the pressure loss inside the tube may become larger, and the water pressure in the vicinity of the tube inlet may become higher than the water pressure in the vicinity of the outlet, which may tend to cause a difference in the heat exchange amount between the vicinity of the inlet and the vicinity of the outlet. Accordingly, the flow speed is preferably 4.0 m/s or less.

It is preferable to pressurize the water to be supplied to the tube side of the submerged condenser with use of a pump. Hence, it is easy to feed a large amount of water (a gas-liquid two-phase flow at the outlet of the tube side) to the tube side. It is also easy to provide an adequate pressure loss to the U-tubes, and to uniformly distribute water to the plurality of U-tubes (prevention of channeling). In the vertical submerged condenser in particular, the U-tubes extend vertically, and therefore it is necessary that the gas-liquid two-phase flow should flow downward. In such a case, pressurization with the pump is effective.

It is possible to perform a gas liquid separation step of performing gas liquid separation of a fluid, this fluid being obtained from the tube side of the submerged condenser, to obtain steam (a stream of steam) and water (a stream of water). Furthermore, it is possible to supply the water obtained in the gas liquid separation step to the tube side of the submerged condenser. In short, water can be separated from the fluid discharged from the U-tubes, and the water can be returned to the U-tubes. For this returning, the aforementioned pump can be used.

As the water to be supplied to the U-tubes of the submerged condenser for generating steam, steam condensate, especially low-pressure steam condensate, can be used. As the steam condensate, steam condensate formed by condensation of appropriate steam in the apparatus for urea production can be used, after being reduced in pressure or being pressurized as necessary. The pressure of the low-pressure steam condensate supplied to the U-tubes is at the same level as that of the low-pressure steam generated in the condensation step. The temperature of the low-pressure steam condensate is at the same level as that of the low-pressure steam generated in the condensation step, and is typically 134° C. to 175° C., preferably 144° C. to 165° C.

Recycling Step

A liquid (absorption medium which has absorbed at least a part of the decomposer outlet gas) obtained from the shell side in the condensation step is sent back to the synthesis step. Thus, unreacted ammonia and unreacted carbon dioxide which were not converted into urea are circulated through the synthesis step, the decomposition step, and the condensation steps. In one of the methods for recycling the condensed liquid obtained in the condensation step, a synthesis reactor for performing the synthesis step is arranged below, and a submerged condenser for performing the condensation step is disposed above the synthesis reactor so as to recycle the condensed liquid using gravity. In another recycling method, the condensed liquid obtained in the condensation step is pressurized with use of an ejector in order to recycle the condensed liquid, where raw material ammonia to be supplied to a synthesis reactor is used as a driving fluid of the ejector. The recycling method using gravity and the recycling method using an ejector may be used in combination.

Others

The present invention is effective in the case of using a vertical submerged condenser in particular. In the vertical submerged condenser using a U-tube, the first-half passage (a passage from the inlet to the U-shaped portion) of the U-tube and the latter-half passage (a passage from the U-shaped portion to the outlet) of the U-tube are located at the same horizontal level. The latter-half passage is higher in the ratio of steam in the cooling medium than the first-half passage. Therefore, a temperature difference may be generated in a horizontal direction, which tends to cause larger temperature distribution inside the submerged condenser. The present invention can reduce such temperature distribution.

When U-tubes are used, only one tubesheet is necessary for the submerged condenser. This is economically advantageous. Further, in the vertical submerged condenser, the tubesheet is preferably provided not on the upper side but on the lower side of the U-tubes, from a viewpoint of easy maintenance.

Since the urea synthesis reaction progresses also in the condensation step, the condensation step and the synthesis step can be carried out in a single pressure vessel. In other words, it is possible to use a single pressure vessel in which a submerged condenser and a synthesis reactor are integrated.

Process Examples

The present invention will be described below in detail with reference to the drawings, but the present invention is not limited thereto.

As shown in FIG. 1, raw material ammonia is pressurized with a pump (not shown) as appropriate, and is supplied to a synthesis reactor A via lines 101, 102, and 103. Raw material carbon dioxide is supplied to the synthesis reactor A via lines 105 and 106. The raw material ammonia (line 101) is heated with use of a heating medium in a heat exchanger (ammonia preheater) E. As the heating medium, an appropriate fluid, such as steam or steam condensate, can be used. For example, steam (line 202) obtained from a submerged condenser C is supplied as the heating medium to the heat exchanger E, so that steam condensate formed by condensation of this steam can be obtained from the heat exchanger E. The raw material ammonia (line 102), which has been heated in this way, can be utilized as a driving fluid of an ejector D.

A urea synthesis solution is sent from the synthesis reactor A to a decomposer B via a line 110. The urea synthesis solution is heated by a heating medium in a heating section (heat exchange structure) of the decomposer B. An appropriate fluid, such as steam or steam condensate, can be used as the heating medium. Typically, medium-pressure steam can be used as the heating medium, and medium-pressure steam condensate formed by condensation of the medium-pressure steam can be withdrawn from the heating section. Carbon dioxide is supplied to the bottom of the decomposer B as a stripping gas, via the line 105 and a line 107.

A decomposer outlet gas is introduced from the decomposer B to the submerged condenser C via a line 112. A urea synthesis solution separated from the decomposer outlet gas is withdrawn from a line 111. Product urea can be obtained by treating, as appropriate, the liquid of the line 111 in the steps publicly known in the field of urea production, such as purification, concentration, and granulation.

The decomposer outlet gas introduced into the submerged condenser C is absorbed and condensed in an absorption liquid (absorption medium) introduced from a line 120. The obtained liquid flows via a line 121 to the ejector D, where the liquid is pressurized, and the liquid is recycled to the synthesis reactor A via the line 103. The gas which was not condensed is withdrawn from a line 122. The gas in the line 122 can be recovered as a recovery liquid, when the gas is absorbed in an absorption medium and when the adsorption medium is simultaneously cooled (not shown). As the absorption medium, an absorption medium publicly known in the field of the process for urea production, such as water (which may contain urea, ammonia, carbon dioxide, and ammonium carbamate), can appropriately be used. The recovered liquid may be pressurized as necessary, and may be utilized as the absorption medium in the condenser C.

Steam condensate is introduced as a cooling medium (water) into the tube side of the submerged condenser C from a line 201. The steam condensate is heated through heat exchange with the fluid on a shell side of the submerged condenser C, and steam is generated.

A recycling means for recycling at least a part of the liquid obtained from the shell side of the submerged condenser C to the synthesis reactor A includes the lines 121, 103, and the ejector D.

A cooling system of the submerged condenser will be described with reference to FIG. 2. When water is supplied to the tube side of the submerged condenser C from the line 201, a part of the water turns into steam, and a gas-liquid two-phase flow is withdrawn from the line 202. The gas liquid separation of the gas-liquid two-phase flow is performed in a gas liquid separator F such that the gas-liquid two-phase flow is separated into steam condensate (line 203) and steam (line 204). The steam condensate of the line 203 is pressurized with a pump G, and is returned to the line 201. Since steam is withdrawn from the line 204, make-up water is supplied to the cooling system from a line 205. In FIG. 2, the make-up water is supplied to the gas liquid separator F.

A water supply means for supplying water to the tube side of the submerged condenser C at a mass flow rate that is three times or more of the steam generation rate includes the lines 201, 202, 203 and 205, the gas liquid separator F, and the pump G. These lines and devices are designed such that water can be supplied to the tube side of the submerged condenser C at a mass flow rate that is three times or more of the steam generation rate.

The steam of the line 204 may be supplied to, for example, a steam turbine H or another device I which consumes the steam, or may be discharged to the atmosphere, after being reduced in pressure as necessary. Steam may be supplied to the line 204 from another device J which generates steam. The another device I which consumes steam and the another device J which generates steam may be present in the apparatus for urea production, or may be present out of the apparatus for urea production. Examples of the another device I which is present in the apparatus for urea production and which consumes steam include the ammonia preheater E. Examples of the another device J which is present out of the apparatus for urea production and which generates steam include an ammonia production plant.

The pressure of the steam generated on the tube side of the submerged condenser C can be controlled so that the heat exchange amount in the submerged condenser C can be adjusted depending on the load (plant load) of the apparatus for urea production, in other words, so that the temperature on the shell side can be adjusted, while supplying excessive steam condensate to the tube side of the submerged condenser C. Examples of specific processes therefor are as shown below.

Increase or decrease the amount of steam supplied to the line 204 from the another device J which generates steam.

Increase or decrease the amount of steam supplied from the line 204 to the another device I which consumes steam.

Increase or decrease the amount of steam supplied to the steam turbine H from the line 204.

Increase or decrease the amount of the steam which is discharged to the atmosphere from the line 204.

For example, as shown in FIG. 2, it is preferable to dispose a dedicated pump G which is used only for supplying water to the tube side of the submerged condenser. In this case, during normal operation, since there is no other place to which the steam condensate is sent than the submerged condenser, the flow rate of the steam condensate (line 201) supplied to the submerged condenser is constant. In other words, it is possible to prevent fluctuation of the flow rate of the steam condensate supplied to the submerged condenser due to fluctuation of the flow rate of the steam condensate supplied to any other place than the submerged condenser. Therefore, heat can reliably be removed from the submerged condenser. In order to promote the urea synthesis reaction in the submerged condenser, the temperature of the submerged condenser is an important parameter in a urea production process. When the flow rate of the steam condensate supplied as a cooling medium to the submerged condenser is constant, it is easy to keep the temperature of the submerged condenser constant. However, blowdown can be performed in order to prevent accumulation of some constituents in the water supply means including the lines 201, 202 and 203. In unsteady operation, delivery of water to devices other than the submerged condenser may be performed besides the blowdown.

REFERENCE SIGNS LIST

A SYNTHESIS REACTOR
B DECOMPOSER
C SUBMERGED CONDENSER
D EJECTOR
E HEAT EXCHANGER (AMMONIA PREHEATER)
F GAS LIQUID SEPARATOR
G PUMP
H STEAM TURBINE
I ANOTHER DEVICE WHICH CONSUMES STEAM
J ANOTHER DEVICE WHICH GENERATES STEAM

The invention claimed is:

1. A process for urea production, comprising:
a synthesis step of synthesizing urea from ammonia and carbon dioxide to generate a urea synthesis solution;
a decomposition step of, by heating the urea synthesis solution generated in the synthesis step, decomposing ammonium carbamate and separating a gaseous mixture containing ammonia and carbon dioxide from the urea synthesis solution to obtain a urea synthesis solution which is higher in urea concentration than the urea synthesis solution obtained in the synthesis step;
a condensation step of, with use of a submerged condenser including a shell and tube heat exchange structure including a U-tube, absorbing and condensing at least a part of the gaseous mixture obtained in the decomposition step in an absorption medium on a shell side, and generating steam on a tube side with use of heat generated during the condensation;
a recycling step of recycling at least a part of a liquid, said liquid being obtained from the shell side in the condensation step, to the synthesis step; and
a water supply step of supplying water to the tube side of the submerged condenser at a mass flow rate that is three times or more of a generation rate of the steam generated in the submerged condenser.

2. The process for urea production according to claim 1, wherein
a flow speed of the water supplied to the tube side of the submerged condenser is 0.3 m/s or more at an inlet of the U-tube.

3. The process for urea production according to claim 1, wherein
the water supply step includes a step of pressurizing the water to be supplied to the tube side of the submerged condenser with use of a pump.

4. The process for urea production according to claim 1, wherein
the water supply step includes a gas liquid separation step of performing gas liquid separation of a fluid, said fluid being obtained from the tube side of the submerged condenser, to obtain steam and water.

5. The process for urea synthesis production according to claim 4, wherein
the water supply step includes a step of supplying the water obtained in the gas liquid separation step to the tube side of the submerged condenser.

6. The process for urea production according to claim 1, wherein
the submerged condenser is a vertical submerged condenser.

7. The process for urea production according to claim 6, wherein
the vertical submerged condenser has a tubesheet provided below the U-tube.

8. The process for urea production according to claim 1, wherein
the mass flow rate of the water supplied to the tube side of the submerged condenser is eight times or more of the generation rate of the steam generated in the submerged condenser.

9. The process for urea production according to claim 1, wherein
the synthesis step and the condensation step are performed in a single pressure vessel.

* * * * *